(12) United States Patent
Salzer et al.

(10) Patent No.: US 8,455,671 B2
(45) Date of Patent: Jun. 4, 2013

(54) RUTHENIUM COMPLEXES WITH (P—P)-COORDINATED FERROCENYLDIPHOSPHINE LIGANDS, PROCESS FOR PREPARING THEM AND THEIR USE IN HOMOGENEOUS CATALYSIS

(75) Inventors: Albrecht Salzer, Aachen (DE); Angelino Doppiu, Seligenstadt (DE); Nadine Langenscheidt, Aachen (DE); Andreas Rivas-Nass, Schriesheim (DE); Ralf Karch, Kleinostheim (DE); Roland Winde, Frankfurt (DE); Stefanie Mayrhofer, Bruchkoebel (DE)

(73) Assignee: Umicore AG & Co. KG, Hanau-Wolfgang (DE)

( * ) Notice: Subject to any disclaimer, the term of this patent is extended or adjusted under 35 U.S.C. 154(b) by 521 days.

(21) Appl. No.: 12/599,077

(22) PCT Filed: May 8, 2008

(86) PCT No.: PCT/EP2008/003695
§ 371 (c)(1),
(2), (4) Date: Oct. 15, 2010

(87) PCT Pub. No.: WO2008/138540
PCT Pub. Date: Nov. 20, 2008

(65) Prior Publication Data
US 2011/0021798 A1    Jan. 27, 2011

(30) Foreign Application Priority Data
May 10, 2007   (DE) .......................... 10 2007 022 389

(51) Int. Cl.
    C07F 15/00    (2006.01)
(52) U.S. Cl.
    USPC ............................................. 556/14; 556/16
(58) Field of Classification Search
    USPC ..................................... 556/14, 16
    See application file for complete search history.

(56) References Cited

U.S. PATENT DOCUMENTS

| | | | |
|---|---|---|---|
| 6,169,192 B1 | 1/2001 | Pugin | |
| 6,191,284 B1 | 2/2001 | Knochel et al. | |

FOREIGN PATENT DOCUMENTS

| | | |
|---|---|---|
| DE | 19952348 A1 | 6/2000 |
| DE | 69820205 T2 | 9/2004 |
| WO | 9852687 | 11/1998 |
| WO | 03976451 A | 9/2003 |
| WO | 2004099226 A1 | 11/2004 |
| WO | 2006067412 A | 6/2006 |
| WO | 2006108562 A | 10/2006 |
| WO | 2007005550 A | 1/2007 |

OTHER PUBLICATIONS

Dai et al., Journal of Molecular Catalysis, vol. 209, No. 1-2, pp. 19-22 (2004).*
Dobbs, et al. Industrielle Synthese von (+)-cis-Methyldihydrojasmonat durch enantioseletive katalytische Hydrierung; Identifizierung des Prakatalysators [Ru((-)-Me-DuPHOS) (H)-n6-1,3,5-cyclooctatrien)](BF4)** Angewandte Chemie, vol. 112. Issue 11, (Jun. 2, 2000), pp. 2080-2083.
Sato, M. and Asai, M.; "Synthetic studies of permethylcyclopentadienyl ruthenium(II) complexes involving dppf, (±)-BINAP and (±)-DIOP ligands". Journal of Organometallic Chemistry, vol. 508, Issues 1-2, (Feb. 8, 1996), pp. 121-127.
Lai Yoong Goh et al.; "Comparative reactivity studies of dppf-containing CpRuII and (C6Me6)RuII complexes towards different donor ligands (dppf=1,1'-bis(diphenylphosphino)ferrocene)" Journal of Organometallic Chemistry, vol. 689, Issue 11, (Jun. 1, 2004), pp. 1978-1990.
Weissensteiner et al. : "Hydrogen-transfer catalyzed by half-sandwich Ru(II) aminophosphine complexes". J. Chem. Soc,. Dalton Trans., 2001, pp. 2989-2995.
Sturm et al. "A Novel Class of Ferrocenyl-Aryl-Based Diphosphine Ligands for Rh- and Ru-Catalysed Enantioselective Hydrogenation". Adv. Synth., Catal. 2003, 345, No. 1+2.
Cayuela, Ester et al. "Monocyclopentadienylhydride derivatives of ruthenium:Stereoselective Proton Transfer and Proton-Hydride Exchange i n an Extremely Short Dihydrogen Bond, "Journal of the American Chemical Society, 2004, vol. 126, pp. 7049-7062, (2004).
Database Chemcats [online] Chemical abstracts service. XP002492362, Accession Nos. 2050381291, 2050381288, 2050381287, 2050381286, All Published Jul. 18, 2008.
Moberg, Viktor et al. "Unprecedented Enantioselectivity in a Cluster-Based Catalytic System" Organometallics, vol. 26, No. 17, pp. 4090-4093 (2007).
International Search Report (PCT/EP2008/003695) Dated Aug. 15, 2008.
Written Opinion (PCT/EP2008/003695) Dated Aug. 15, 2008.
Geldbach, Tilmann, et al., Organometallics 2005, 24, 4974-4980.
Zanetti, Nadia, et al., Organometallics 1996, 15, 860-866.
Search Report for Chinese Application No. 200880015440.7.

* cited by examiner

Primary Examiner — Porfirio Nazario Gonzalez
(74) Attorney, Agent, or Firm — Levin Santalone LLP; John Santalone

(57) ABSTRACT

The invention relates to ruthenium complexes with a chiral ferrocenyldiphosphine ligand, wherein the ruthenium has the oxidation state (+II) and the chiral ferrocenyldiphosphine ligand has bidentate P—P coordination to the ruthenium. The ruthenium complexes are cyclic and with the ferrocenyldiphosphine ligand have an at least eight-membered ring. The ferrocenyldiphosphine ligands are selected from the group consisting of Taniaphos, Taniaphos-OH and Walphos ligands. A process for preparing the Ru complexes is described. The Rn complexes are used as catalysts for homogeneous asymmetric catalysis for preparing organic compounds.

21 Claims, No Drawings

RUTHENIUM COMPLEXES WITH (P—P)-COORDINATED FERROCENYLDIPHOSPHINE LIGANDS, PROCESS FOR PREPARING THEM AND THEIR USE IN HOMOGENEOUS CATALYSIS

FIELD OF THE INVENTION

The present invention relates to ruthenium complexes for homogeneous catalysis. In particular, the invention relates to ferrocene-containing, P—P-coordinated ruthenium complexes with chiral diphosphine ligands (known as ferrocenyldiphosphine ligands) and a process for preparing them. The invention further relates to the use of these complexes as catalysts for homogeneous catalytic hydrogenation.

BACKGROUND OF THE INVENTION

Chiral ferrocenyldiphosphines have proven to be valuable ligands for catalytically active metal complexes which are used in homogeneous catalysis for the enantioselective hydrogenation of organic compounds. Fields of use are the preparation of intermediates or active compounds, for example pharmaceuticals, pesticides, flavors or fragrances.

Among the diphosphines having a ferrocene framework, 1-sec-phosphino-2-(2'-sec-phosphino-1-benzyl)-ferrocenes, for example, have proven to be valuable ligands for noble metal complexes for the enantioselective hydrogenation of organic compounds. Ligands of this type are referred to by the name "Taniaphos" and are described in WO 00/37478. Further examples of diphosphines having a ferrocene framework are 1-(α-sec-phosphinoalkyl)-2-(sec-phosphinoaryl)-ferrocenes which are disclosed in WO 02/02578 (trivial name "Walphos").

In enantioselective hydrogenation, these diphosphine ligands are used together with suitable noble metal complexes. The reaction of asymmetric ferrocenyldiphosphine ligands with organometallic Ru compounds leads to mixtures of complexes which have monodentate coordination of the P atoms of the phosphine ligand, cf. equ. (1):

Equation (1):

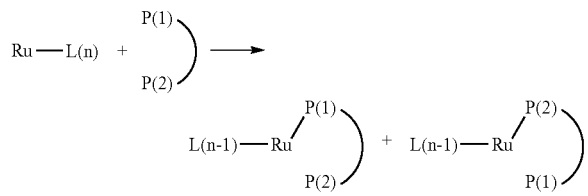

According to equ. (1), an isomer mixture of monodentate, P-coordinated Ru complexes in which in each case, only one of the P atoms of the ferrocenyldiphosphine ligand is bound to the ruthenium is present. The two isomers in equation (1) can be distinguished, for example, by means of $^{31}$P-NMR spectroscopy. Simultaneous coordination of both P atoms of the ferrocenyldiphosphine ligand in a ruthenium complex (hereinafter referred to as "bidentate" coordination or "P—P coordination") has hitherto not been observed.

Organometallic Ru compounds used in these hydrogenations are, for example, $[Ru(COD)Y_2]_x$, $[Ru(NBD)Y_2]_x$, $[Ru(aromatic)Y_2]_x$ or $[Ru(COD)(2-methylallyl)_2]$ (where X=2; Y=halide, COD=1,5-cyclooctadiene, NBD=norbornadiene, aromatic=for example, p-cumene or another benzene derivative).

EP 1622920B1 discloses transition metal complexes with ferrocenyldiphosphine ligands. Complexes having specific P—P coordination of the phosphine ligands are not described, and in addition the diphosphine ligands disclosed have phosphine groups which are located on different ferrocene rings of the ligand system.

Although WO 00/37478 describes transition metal complexes which contain a metal atom of transition group 7 or 8 and in which both P atoms of the ferrocenyldiphosphine ligand are simultaneously coordinated to the central atom, the complexes are neither isolated nor characterized. No process for preparing them is described; rather, the complexes are generated shortly before use by combining the ligands and the appropriate transition metal salts in the reaction solvent ("in situ").

These in-situ processes are prior art. Thus, ferrocenyldiphosphine ligands are reacted with ruthenium complexes in an in-situ procedure; cf. Angewandte Chemie 1999, 111, No. 21, 3397-3400. Here, $[Ru(COD)(C_4H_7)_2]HBr$ (COD=cycloocta-1,5-diene, $C_4H_7=2-(\eta^3-)$methylallyl) is used as Ru complex and β-keto esters of the type R—CO—$CH_2$—CO—OEt are hydrogenated in ethanol at 50° C. under 50 bar of hydrogen. The same Ru starting compound is used in Tetrahedron Asymmetry 15 (2004) 91-102 and the catalyst is prepared in situ.

Adv. Synth. Catal. 2003, 345, 160-164 describes phenylferrocenylethyldiphosphine ligands of the "Walphos" type. Dimeric $[RuI_2(p\text{-cumene})]_2$ is used as Ru-containing catalyst precursor in the hydrogenation and the catalyst is formed in situ.

However, no studies on the structure of the metal complexes generated in situ have hitherto been carried out; the corresponding complexes were not isolated but used directly in the reaction mixture for homogeneous catalysis, in particular for catalytic hydrogenation.

Disadvantages of the catalytic hydrogenation processes which have been described up to now and the catalysts used therein are, in particular, the low enantio-selectivities and a high consumption of noble metal catalysts, i.e. a low substrate/catalyst (S/C) ratio, and long hydrogenation times.

SUMMARY OF THE INVENTION

It was therefore an object of the present invention to provide improved catalysts for homogeneous, asymmetric hydrogenation.

This object is achieved by provision of the ruthenium complexes of the types (A) and (B) as claimed in claim 1 of the invention. Furthermore, a process for preparing the complexes of the invention is disclosed in claim 11. Preferred embodiments are described in the subordinate claims dependent thereon.

The present invention describes ruthenium complexes with a chiral ferrocenyldiphosphine ligand for homogeneous catalysis, wherein the ruthenium has the oxidation state (+II) and the ferrocenyldiphosphine ligands have bidentate P—P coordination to the Ru. The ruthenium complexes are cyclic and with the ferrocenyldiphosphine ligand have an at least eight-membered ring. The ferrocenyldiphosphine ligands are, for example, selected from the group consisting of "Taniaphos" and "Walphos" ligands, but are not restricted to these ligands.

The present invention further provides a process for preparing the ruthenium complexes of the invention, in which specific Ru starting compounds are reacted with a chiral ferrocenyldiphosphine ligand.

DETAILED DESCRIPTION OF THE PREFERRED EMBODIMENTS

In the search for well-defined Ru complexes with ferrocenyldiphosphine ligands, it has surprisingly been found that simultaneous coordination of both P atoms of the ferrocenyldiphosphine ligands to a central Ru atom can be achieved under particular conditions. This gives cyclic Ru complexes which have an at least eight-membered ring in their structure (number of ring members r≧8).

The effect of P—P coordination is obtained by use of specific ferrocenyldiphosphine ligands which have at least seven ring-forming atoms in their structure and are therefore sterically capable of forming an at least eight-membered ring with the central Ru atom. The phosphino groups are preferably located on one (i.e. on the same) cyclopentadienyl ring of the ferrocene molecule.

Examples of suitable ferrocenyldiphosphine ligands are ligands of the Taniaphos type and their derivatives, for example Taniaphos-OH or Taniaphos-OMe, etc. However, it is also possible to use ligands of the "Walphos" type. Examples of suitable ferrocenyldiphosphine ligands for preparing the Ru complexes of the invention are:

(S)-1-diphenylphosphino-2-[(R)-α-(N,N-dimethylamino)-o-(diphenylphosphinophenyl)methyl]ferrocene (=Taniaphos T001-1)

(R)-1-diphenylphosphino-2-[(S)-α-(N,N-dimethylamino)-o-(diphenylphosphinophenyl)methyl]ferrocene (=Taniaphos T001-2)

(S)-1-dicyclohexylphosphino-2-[(R)-α-(N,N-dimethylamino)-o-(dicyclohexylphosphinophenyl)methyl]ferrocene (=Taniaphos T002-1)

(R)-1-dicyclohexylphosphino-2-[(S)-α-(N,N-dimethylamino)-o-(dicyclohexylphosphinophenyl)methyl]ferrocene (=Taniaphos T002-2);

(S)-1-diphenylphosphino-2-[α-(S)-hydroxy-(o-diphenylphosphinophenyl)methyl]ferrocene ("Taniaphos OH"); and derivatives of this type;

(S)-1-diphenylphosphino-2-[α-(S)-methoxy(o-diphenylphosphinophenyl)methyl]ferrocene ("Taniaphos OMe"); and derivatives of this type (cf. WO 2003/076451);

(R)-1-[(R)-2-(2'-diphenylphosphinophenyl)ferrocenyl]ethyldi(bis-3,5-trifluoromethylphenyl)phosphine (Walphos W001-1);

(S)-1-[(S)-2-(2'-diphenylphosphinophenyl)ferrocenyl]ethyldi(bis-3,5-trifluoromethylphenyl)phosphine (Walphos W001-2);

(R)-1-[(R)-2-(2'-diphenylphosphinophenyl)ferrocenyl]ethyldiphenylphosphine (Walphos W002-1);

(S)-1-[(S)-2-(2'-diphenylphosphinophenyl)ferrocenyl]ethyldiphenylphosphine (Walphos W002-2);

(R)-1-[(R)-2-(2'-diphenylphosphinophenyl)ferrocenyl]ethyldicyclohexylphosphine (Walphos W003-1);

(S)-1-[(S)-2-(2'-diphenylphosphinophenyl)ferrocenyl]ethyldicyclohexylphosphine (Walphos W003-1);

(R)-1-[(R)-2-(2'-di(3,5-dimethyl-4-methoxyphenyl)phosphinophenyl)ferrocenyl]ethyldi(bis-3,5-trifluoromethyl) phenyl)phosphine (Walphos W005-1);

(S)-1-[(S)-2-(2'-di(3,5-dimethyl-4-methoxyphenyl)phosphinophenyl)ferrocenyl]ethyldi(bis-3,5-trifluoromethylphenyl)phosphine (Walphos W005-2);

(R)-1-[(R)-2-(2'-diphenylphosphinophenyl)ferrocenyl]ethyldi(3,5-xylyl)phosphine (Walphos W006-1);

(S)-1-[(S)-2-(2'-diphenylphosphinophenyl)ferrocenyl]ethyldi(3,5-xylyl)phosphine (Walphos W006-2);

(R)-1-[(R)-2-(2'-dicyclohexylphosphinophenyl)ferrocenyl] ethyldi(3,5-trifluoromethyl)phenyl)phosphine (Walphos W008-1);

(S)-1-[(S)-2-(2'-dicyclohexylphosphinophenyl)ferrocenyl] ethyldi(3,5-trifluoromethyl)phenyl)phosphine (Walphos W008-2).

These chiral ferrocenyldiphosphine ligands are in most cases commercially available. Use of these ligands in the preparative process of the invention gives cyclic Ru complexes which have an eight-membered ring in their structure. However, other chiral ferrocenyldiphosphine ligands are also suitable as long as they allow formation of an at least eight-membered ring (number of ring members r≧8).

In the present preparative process, the effect of P—P coordination is achieved by use of specific Ru starting compounds which are present in the oxidation state (+II) and have at least two neutral 2-electron donor ligands $L_D$. They have the following general formula

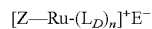

$$[Z—Ru-(L_D)_n]^+E^-$$

where

Ru is in the oxidation state +II, n is an integer equal to or greater than 3, $L_D$ is an neutral ligand, Z is at least one π-bonded organic ligand and $E^-$ is the anion of an oxo acid or complex acid.

The at least three neutral ligands $L_D$ generally belong to the class of 2-electron donor ligands such as secondary or tertiary phosphines or N-heterocyclic carbene ligands (known as NHC ligands). The ligands $L_D$ are preferably solvent ligands which are bound to the central Ru atom. At least two of these ligands are replaced in the reaction by a chiral diphosphine ligand. Examples of suitable ligands $L_D$ are ligands from the group consisting of alcohols, ethers, amines, acid amides, lactams and sulfones; for example acetonitrile ($CH_3CN$), diethyl ether (DEE), water ($H_2O$) or acetone. It is also possible to use cyclic ligands such as tetrahydrofuran (THF), dioxane, pyridine, imidazole or thiophene. Mixed systems having different types of ligands, for example ones containing phosphine ligands and/or carbene ligands and/or solvent ligands, are also possible.

Furthermore, the Ru starting compound has at least one π-bonded organic ligand Z. Z encompasses substituted or unsubstituted cyclic or open-chain dienyl ligands in general, for example substituted or unsubstituted pentadienyl or heptadienyl ligands.

For clarification, such dienyl ligands are, when bonded to the Ru, negatively charged, i.e. anionic.

Preference is given to using 2,4-dimethylpentadiene, 2,3,4-trimethylpentadiene, cycloheptadiene, cyclooctadiene, norbornadiene, etc. The ligands Z can also be present in the protonated state and have protons in an "agostic interaction".

Most preferably, for Z, one negatively charged open-chain dienyl ligand, for example 2,4-dimethylpentadienyl- or 2,3,4-trimethylpentadienyl- is employed.

The Ru starting compound is present as cation having a single positive charge and has, as further constituent the anion of an oxo acid or complex acid as counterion. Examples of $E^-$ are $HSO_4^-$, $CF_3SO_3^-$, $ClO_4^-$, $BF_4^-$, $B(aryl)_4^-$, $SbF_6^-$ and $PF_6^-$.

Examples of suitable Ru starting compounds are $[Ru(2,4\text{-dimethylpentadienyl})(CH_3CN)_3]^+BF_4^-$ or $[Ru(2,4\text{-dimethylpentadienyl})(acetone)_3]^+BF_4^-$.

The Ru starting compound can be prepared in various process steps from known Ru precursor compounds by reaction with the appropriate ligand $L_D$ and isolated. The Ru precursor compound can be protonated before reaction with the neutral ligand $L_D$ in order to achieve improved ligand replacement by L.

As Ru precursors, it is possible to use the compounds mentioned above, e.g. bis(η5-(2,4-dimethylpentadienyl)Ru, [Ru(COD)Cl$_2$]$_2$, [Ru(norbornadiene)Cl$_2$]$_2$, [Ru(p-cumene)I$_2$]$_2$ or [Ru(COD)(2-methylallyl)$_2$]. These Ru compounds are commercially available. The preparation procedures for the Ru starting compound have to be adjusted depending on the precursor compound used.

A preferred Ru precursor comprises negatively charged Z ligands, such as, for example, bis(η5-(2,4-dimethylpentadienyl)Ru. The preparation of the Ru starting compound typically proceeds in two steps:

Step A (Protonation):

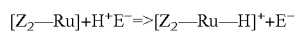

Step B (Ligand Exchange):

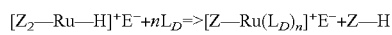

It has been found that reaction of the Ru starting compounds with the appropriate chiral ferrocenyldiphosphine ligands (hereinafter represented as P(1)-P(2) for short) gives the Ru complexes of the invention. The formation of the ferrocenyldiphosphine complex then occurs in step C. The preparative process of the invention is shown in general form in equ. (2):

Step C (Ligand Exchange According to Equation (2)):

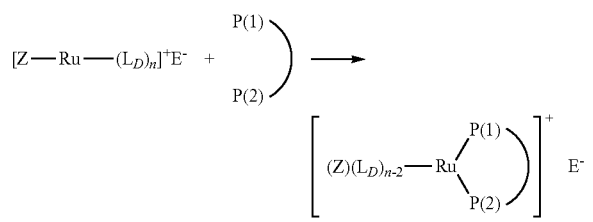

The reaction of equ. (2) gives the novel Ru complexes of type (A). To prepare the Ru complexes of type (A), the ferrocenyldiphosphine ligands are reacted with the above-described Ru starting compound, resulting in at least two of the ligands $L_D$ being replaced by the chiral diphosphine ligands in the reaction. If the Ru starting compound has more than two ligands $L_D$, the remaining ligands $L_D$ remain coordinated to the ruthenium. They can be replaced or eliminated in a subsequent step. The preparation of the Ru complexes is preferably carried out under a protective gas atmosphere using the Schlenk technique and oxygen-free solvents. The ferrocenyldiphosphine ligands are typically reacted with the Ru starting compound in a suitable solvent at temperatures in the range from 20 to 80° C., preferably in the range from 20 to 60° C. and particularly preferably at room temperature (25° C.), while stirring. Suitable solvents are chlorinated hydrocarbons such as chloroform, methylene chloride, trichloroethane or dichloroethane. The reaction times range from 1 hour to 10 hours. It can be advantageous to use the ligand in a small excess in the preparation of the Ru complexes. The excess can be in the range from 1 to 10 mol % (based on the Ru starting compound). The subsequent isolation, washing and purification steps are well known to those skilled in the art. To remove solvent residues, the product is dried under reduced pressure.

In a further embodiment, the present invention encompasses Ru complexes of type (B). These complexes bear no net charge and have a negatively charged ligand $L_Z$ in addition to the P—P-coordinated ferrocenyldiphosphine ligand, the π-bonded organic ligand Z and, if appropriate, the ligand $L_D$.

This ligand $L_Z$ can be introduced by replacement of one of the ligands $L_D$ by a halide ion (fluoride, chloride, bromide or iodide) or a pseudohalide ion (e.g. CN$^-$, SCN$^-$, cyanate, isocyanate, etc.). The Ru complex of type (B) is preferably prepared from the complex of type (A) by subsequent ligand exchange, for example by replacement of an acetonitrile molecule by iodide (cf. example 2):

Step D (Replacement of the Ligand $L_D$ by Negatively Charged Ligands $L_Z$) According to equ. (3).

Equation (3):

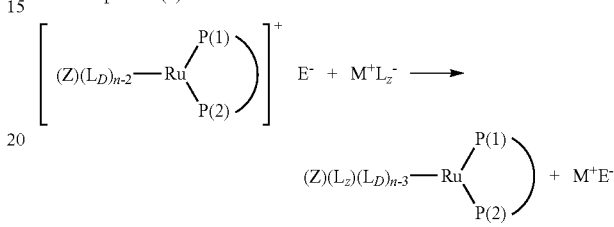

To carry out step D, the cationic Ru complex (type A) is dissolved in a dipolar, aprotic solvent, for example acetone or THF, and reacted with ligand $L_Z$ at temperatures in the range from 20 to 50° C. The product generally precipitates and can be separated off.

The novel Ru complexes of type (A)

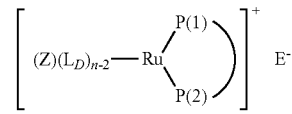

and type (B)

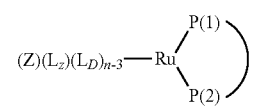

where, in each case,
Ru is in the oxidation state +II,
n is an integer equal to or greater than 3,
$L_D$ is an neutral ligand,
Z is at least one π-bonded organic ligand,
E$^-$ is an anion of an oxo acid or complex acid and
$L_Z$ is at least one anionic ligand
and the ferrocenyldiphosphine ligand P(1)-P(2) has bidentate P—P coordination, are effective homogeneous catalysts for the asymmetric hydrogenation of prochiral organic compounds.

They are therefore used as catalysts for homogeneous asymmetric catalysis, for example for the enantio-selective hydrogenation of multiple bonds. For the purposes of the present invention, multiple bonds are double bonds between a carbon atom and a further carbon atom (C=C) or oxygen atom (C=O) or nitrogen atom (C=N).

Furthermore, the ruthenium complexes of the invention can also be used as catalysts for other asymmetric reactions. These include C—C, C—O, C—N, C—P, C—Si, C—B or C-halogen bond formation reactions. Examples are asymmetric cyclization reactions, asymmetric oligomerizations and asymmetric polymerization reactions.

The novel Ru complexes of type (A) and (B) are used as defined compounds and display, for example, very good catalytic properties in hydrogenation. In comparison, Ru complexes which only have single, monodentate coordination of the P atoms of the ferrocenyldiphosphine ligands or Ru compounds which are used together with the ferrocenyldiphosphine ligands in the in-situ process display poorer catalytic properties.

The following examples illustrate the invention.

EXAMPLES

Example 1

Preparation of (η5-2,4-dimethylpentadienyl)-
(CH$_3$CN)-(Taniaphos T001-1)ruthenium(II) tetrafluoroborate a) Preparation of (η4-2,4-dimethylpentadiene-η2-C,
H)-(η5-2,4-dimethylpentadienyl)ruthenium tetrafluoroborate In a 100 ml Schlenk tube provided with a magnetic stirrer, 1.1 g (3.77 mmol) of bis(η5-2,4-dimethylpentadienyl)ruthenium (from Colonial Metals Inc., Elkton, Md., USA) are dissolved in 50 ml of diethyl ether. At room temperature, 0.51 ml (3.77 mmol) of a 54% strength HBF$_4$-Et$_2$O solution (from Aldrich) is added dropwise over a period of 10 minutes. After the addition is complete, the mixture is allowed to settle and the completeness of the precipitation is checked by addition of a further drop of HBF$_4$-Et$_2$O. The supernatant solvent is taken off and the solid is washed twice with diethyl ether. The light-yellow residue is dried under reduced pressure. Yield: 1.43 g (100%).

b) Preparation of the Acetonitrile Complex (η5-2,4-dimethylpentadienyl)-(CH$_3$CN)$_3$ruthenium(II) tetrafluoroborate 0.41 g of (1.1 mmol) of (η2,4-dimethylpentadiene-η2-C, H)-η5-2,4-dimethylpentadienyl)ruthenium tetrafluoroborate; prepared in step a), is admixed with 10 ml of acetonitrile. The orange solution is stirred for 10 minutes and the solvent is then removed under reduced pressure to give an orange solid. Yield: 0.44 g (100%).

c) Reaction with Taniaphos T 001-1

Taniaphos SL-T001-1 (from Solvias, Basel, CH; 400 mg, 0.58 mmol) is placed in a round-bottom flask provided with a magnetic stirrer and the Ru starting compound (236 mg, 0.58 mmol) prepared in b) is then added. The reactants are dissolved in 10 ml of CH$_2$Cl$_2$ and the mixture is stirred at room temperature for three hours. The solution becomes deep red. The solvent is taken off under reduced pressure and the solid residue is washed with diethyl ether. The product is collected and dried in a high vacuum. Yield: 90%, red-orange solid, two diastereomers having a de of 75%.
Characterization:
$^1$H NMR (CD$_2$Cl$_2$, major) δ: −1.76 (b, 1H, pentadienyl), 0.15 (b, 1H, pentadienyl), 0.765 (t, 1H, J=6.41 Hz, pentadienyl), 1.24 (b, 3H, pentadienyl-CH$_3$), 1.81 (s, 6H, N(CH$_3$)$_2$), 2.34 (m, 3H, pentadienyl-CH$_3$), 2.88 (s, 3H, CH$_3$CN), 3.63 (b, 1H), 3.66 (m, 1H), 3.76 (s, 5H), 4.39 (t, 1H, J=2.4 Hz), 4.87 (m, 1H), 4.89 (m, 1H), 5.90 (s, 1H), 6.02 (t, 2H), 6.90-8.20 (m, 21H), 8.80 (dd, 1H, J=7.6 Hz, J=14.3 Hz).

$^{31}$P NMR (CD$_2$Cl$_2$) δ: 36.54 (d, J$_{PP}$=34.6 Hz), 31.59 (d, J$_{PP}$=34.6 Hz). $^{19}$F NMR (CD$_2$Cl$_2$) δ: −149.87 (s). The P—P coordination according to the invention is evidenced by the fact that 2 P signals having chemical shifts which are relatively close together (δ: 36.54 ppm (d, J$_{PP}$=34.6 Hz) and 31.59 ppm (d, J$_{PP}$=34.6 Hz)) occur in the $^{31}$P NMR and a coupling between P(1) and P(2) of 34.6 Hz is observed. Signals of a noncoordinated P atom are not found.

The complex according to the invention gives very good yields when used as catalyst for enantioselective catalytic hydrogenation.

Example 2

Preparation of (η5-2,4-dimethylpentadienyl)(iodo)-
(Taniaphos T001-1)ruthenium(II)

The Taniaphos complex (η5-2,4-dimethylpentadienyl)-(CH$_3$CN)(Taniaphos T001-1)ruthenium(II) tetrafluoroborate is prepared as described in example 1c). 100 mg of this compound are dissolved in 4 ml of acetone, an excess of 2 equivalents of potassium iodide (80 mg) is added and the mixture is stirred at room temperature for 10 hours. The precipitated solid is filtered off and washed firstly with water and then with cold acetone. This gives a mixture of two diastereomers having a de of 60% as a yellow-orange solid in a yield of 85%.
Characterization:
$^1$H NMR (CD$_2$Cl$_2$, major) δ: −2.06 (m, 1H), −0.13 (m, 1H), 0.93 (m, 1H), 1.29 (s, 3H), 1.95 (s, 6H), 2.81 (s, 3H), 3.28 (m, 1H), 3.76 (m, 1H), 3.80 (s, 5H), 4.17 (m, 1H), 4.75 (m, 1H), 5.54 (m, 1H), 6.07 (m, 2H), 6.6-7.8 (m, 21H), 9.25 (m, 1H), 9.63 (m, 1H).
$^{31}$P NMR (CD$_2$Cl$_2$) δ: 39.88 ppm (d, J$_{PP}$=40.5 Hz), 29.96 mm (d, J$_{PP}$=40.5 Hz). MS (FAB) m/e: 1012 [M$^+$+1], 884 [M$^+$-I], 788 [M$^+$-I-pentadienyl]. The P—P coordination according to the invention is evidenced by the fact that only 2 P signals having chemical shifts which are relatively close together (δ: 39.88 ppm and 29.96 ppm) occur in the $^{31}$P NMR and a coupling of 40.5 Hz between P(1) and P(2) is observed.
Use for Catalytic Hydrogenation:

The (Taniaphos T001-1)(iodo)ruthenium(II) complex prepared as described in example 2 is used for the asymmetric hydrogenation of trans-2-methyl-2-butenoic acid. The hydrogenation is carried out in an autoclave under 50 bar of hydrogen; solvent: methanol; temperature: 50° C. A little methanolic HCl is added. After a reaction time of 18 hours, the hydrogen pressure is vented. Analysis of the crude material indicates a conversion of >90% and an enantiomeric excess (ee) of >40%. The substrate/catalyst ratio (S/C) is >500.

The complex according to the invention thus gives very good results when used as catalyst for enantioselective catalytic hydrogenation.

Example 3

Preparation of (η5-2,4-dimethylpentadienyl)(iodo)-
(Taniaphos-OH)ruthenium(II)

In a round-bottom flask provided with a magnetic stirrer, the acetonitrile complex (η5-2,4-dimethylpentadienyl)(CH$_3$CN)$_3$ruthenium(II) tetrafluoroborate prepared as described in example 1b) (288 mg, 0.71 mmol) is dissolved in 15 ml of methylene chloride and stirred with (S,S)-Taniaphos-OH (288 mg, 0.71 mmol) at room temperature for 3 hours. The solution becomes deep red. The solvent is removed under reduced pressure and the residue is washed with diethyl ether. The (Taniaphos-OH)ruthenium(II) tetrafluoroborate complex obtained is not isolated further but dissolved in 20 ml of acetone. Excess potassium iodide (330 mg, 2 mmol) is added and the solution is stirred for a further 10 hours. The precipitated yellow-orange solid is filtered off and washed with water and acetone. This gives a product comprising a mixture of two diastereomers in a virtually equimolar ratio. Yield: 90%. The P—P coordination of the Taniaphos-OH ligand is evidenced by the $^{31}$P-NMR.

The Ru complex gives good yields when used as catalyst for enantioselective catalytic hydrogenation.

Comparative Example 1

CE1

Preparation of an Ru Complex with P-monocoordinated ferrocenyldiphosphine Ligands The reaction of Taniaphos SL-T001-1 with the commercially available ruthenium complex [RuCl$_2$(p-cumene)]$_2$ (from Umicore, Hanau) in THF at room temperature gives, in accordance with equ. (1), a 2:1 mixture of two isomers which were identified as P-monocoordinated complexes by means of $^{31}$P spectroscopy. The spectrum displays four different signals ($^{31}$P NMR in CD$_2$Cl$_2$: δ=49 ppm and −13 ppm for the isomer present in the lesser amount, δ=35 ppm and −15 ppm for the predominant isomer). Here, the signals having a negative chemical shift (δ=−13 ppm and −15 ppm) can be assigned to the noncoordinated P atoms of the ligand in each case.

When the mixture is refluxed for 2 hours, the isomer which is present in the predominant proportion is formed; isolation is effected by precipitation with hexane. Bidentate P—P coordination of the ferrocenyl-diphosphine ligand is not observed.

Use for Catalytic Hydrogenation:

The Ru complex mixture prepared as described in comparative example 1 is used for the asymmetric hydrogenation of trans-2-methyl-2-butenoic acid. The hydrogenation is carried out in an autoclave under 50 bar of hydrogen; solvent: methanol; temperature: 50° C. A little methanolic HCl is added. After a reaction time of 18 hours, the hydrogen pressure is vented. Analysis of the crude material indicates incomplete reaction and an ee of <38%. The substrate/catalyst ratio (S/C) is 200.

These results can be compared with the results of example 2. They demonstrate the superiority of the Ru complexes of the invention having P—P coordination of the ferrocenyl-diphosphine ligands in the asymmetric hydrogenation of chiral organic compounds.

What is claimed is:

1. A ruthenium complex with a chiral ferrocenyldiphosphine ligand for homogeneous catalysis corresponding to the general formula

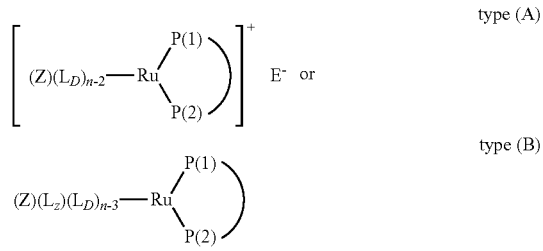

where

Ru is in the oxidation state +II,
n is an integer equal to or greater than 3,
L$_D$ is a neutral ligand,
Z is π-bonded organic ligand,
E$^-$ is an anion selected from the group consisting of HSO$_4$$^-$, CF$_3$SO$_3$$^-$, ClO$_4$$^-$, BF$_4$$^-$, B(aryl)$_4$$^-$, SbF$_6$$^-$ and PF$_6$$^-$ and
L$_z$ is an anionic ligand
and the ferrocenyldiphosphine ligand P(1)-P(2) has bidentate P—P coordination, and together with the ruthenium forms an at least eight-membered ring.

2. The ruthenium complex as claimed in claim 1, wherein the chiral ferrocenyldiphosphine ligand P(1)-P(2) is selected from the group consisting of (S)-1-diphenylphosphino-2-[(R)-α-(N,N-dimethylamino)-o-(diphenylphosphinophenyl)methyl]ferrocene ("Taniaphos T001-1"); (R)-1-diphenylphosphino-2-[(S)-α-(N,N-dimethylamino}-o-(diphenylphosphinophenyl)methyl]ferrocene ("Taniaphos T001-2"); (S)-1-dicyclohexylphosphino-2-[(R)-α-(N,N-dimethylamino)-o-(dicyclohexylphosphinophenyl)methyl]ferrocene ("Taniaphos T002-1"); (R)-1-dicyclohexylphosphino-2-[(S)-α-(N,N-dimethylamino)-o-(dicyclohexylphosphinophenyl)methyl]ferrocene ("Taniaphos T002-2"); (S)-1-diphenylphosphino-2-[α-(S)-hydroxy-(o-diphenylphosphinophenyl)methyl]ferrocene ("Taniaphos OH") and derivatives of this type; (S)-1-diphenylphosphino-2-[α-(S)-methoxy(o-diphenylphosphinophenyl)methyl]ferrocene ("Taniaphos OMe") and derivatives of this type; (R)-1-[(R)-2-(2'-diphenylphosphinophenyl)ferrocenyl]ethyldi(bis-3,5-trifluoromethylphenyl)phosphine ("Walphos W001-1"); (S)-1-[(S)-2-(2'-diphenylphosphinophenyl)ferrocenyl]ethyldi (bis-3,5-trifluoro methylphenyl)phosphine ("Walphos W001-2"); (R)-1-[(R)-2-(2'-diphenylphosphinophenyl)ferrocenyl]ethyldiphenylphosphine ("Walphos W002-1"); (S)-1-[(S)-2-(2'-diphenylphosphinophenyl)ferrocenyl]ethyldiphenylphosphine ("Walphos W002-2"); (R)-1-[(R)-2-(2'-diphenylphosphinophenyl)ferrocenyl]ethyldicyclohexylphosphine ("Walphos W003-1"); (S)-1-[(S)-2-(2'-diphenylphosphinophenyl)ferrocenyl]ethyldicyclohexylphosphine ("Walphos W003-1"); (R)-1-[(R)-2-(2'-di(3,5-dimethyl-4-methoxyphenyl)phosphinophenyl)ferrocenyl]ethlydi(bis-3,5-trifluoromethyl)phenyl)phosphine ("Walphos W005-1"); (S)-1-[(S)-2-(2'-di(3,5-dimethyl-4-methoxyphenyl)phosphinophenyl)ferrocenyl]ethyldi(bis-3,5-trifluoromethylphenyl)phosphine ("Walphos W005-2"); (R)-1-[(R)-2-(2'-diphenylphosphinophenyl)ferrocenyl]ethyldi(3,5-xylyl)phosphine ("Walphos W006-1"); (S)-1-[(S)-2-(2'-diphenylphosphinophenyl)ferrocenyl]ethyldi(3,5-xylyl)phosphine ("Walphos W006-2"); (R)-1-[(R)-2-(2'-dicyclohexylphosphino phenyl)ferrocenyl]ethyldi(3,5-trifluoromethyl)phenyl)phosphine ("Walphos W008-1"); (S)-1-[(S)-2-(2'-dicyclohexylphosphinophenyl)ferrocenyl]ethyldi(3,5-trifluoromethyl)phenyl)phosphine ("Walphos W008-2").

3. The ruthenium complex as claimed in claim 1, wherein L$_D$ is selected from the class of 2-electron donor ligands and encompasses secondary or tertiary phosphines or N-heterocyclic carbine (NHC) ligands.

4. The ruthenium complex as claimed in claim 1, wherein L$_D$ is a solvent ligand selected from the group consisting of acetonitrile (CH$_3$CN), diethyl ether (DEE), water (H$_2$O), acetone, tetrahydrofuran (THF), dioxane, pyridine, imidazole and thiophene.

5. The ruthenium complex as claimed in claim 1, wherein Z is a substituted or unsubstituted cyclic or open-chain dienyl ligand.

6. The ruthenium complex as claimed in claim 1, wherein Z is a ligand selected from the group consisting of 2,4-dimethylpentadiene, 2,3,4-trimethylpentadiene, cycloheptadiene, cyclooctadiene and norbornadiene.

7. The ruthenium complex as claimed in claim 1, wherein $L_z$ is at least one anionic ligand selected from the group consisting of halides and pseudohalides.

8. The ruthenium complex as claimed in claim 1, wherein the chiral ferrocenyldiphosphine ligand is selected from the group consisting of (S)-1-diphenylphosphino-2-[(R)-α-(N,N-dimethylamino)-o-(diphenylphosphino-phenyl)methyl]ferrocene ("Taniaphos T001-1"); (R)-1-diphenylphosphino-2-[(S)-α-(N,N-dimethyl-amino)-o-(diphenylphosphinophenyl)methyl]ferrocene ("Taniaphos T001-2"); (S)-1-dicyclohexylphosphino-2-[(R)-α-(N,N-dimethylamino)(dicyclohexyl-phosphinophenyl)methyl]ferrocene ("Taniaphos T002-1") and (R)-1-dicyclohexylphosphino-2-[(S)-α-(N,N-dimethylamino)(dicyclohexylphosphino phenyl)methyl]ferrocene ("Taniaphos T002-2").

9. A process for preparing ruthenium complexes with a chiral ferrocenyldiphosphine ligand which has bidentate P—P coordination, and together with the ruthenium forms an at least eight-membered ring, characterized in that an Ru starting compound of the general formula

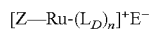

where
Ru is in the oxidation state +II,
n is an integer equal to or greater than 3,
$L_D$ is a neutral ligand,
Z is π-bonded organic ligand and
E⁻ is an anion selected from the group consisting of $HSO_4^-$, $CF_3^-$, $SO_3^-$, $ClO_4^-$, $BF_4^-$, $B(aryl)_4^-$, $SbF_6^-$ and $PF_6^-$,
is reacted with the chiral ferrocenyldiphosphine ligand.

10. The process as claimed in claim 9, wherein the chiral ferrocenyldiphosphine ligand is selected from the group consisting of (S)-1-diphenylphosphino-2-[(R)-α-(N,N-dimethylamino)-o-(diphenylphosphinophenyl)methyl]ferrocene ("Taniaphos T001-1"); (R)-1-diphenylphosphino-2-[(S)-α-(N,N-dimethylamino]-o-(diphenylphosphinophenyl)methyl]ferrocene ("Taniaphos T001-2"); (S)-1-dicyclohexylphosphino-2-[(R)-α-(N,N-dimethylamino)-o-(dicyclohexylphosphinophenyl)methyl]ferrocene ("Taniaphos T002-1") (R)-1-dicyclohexylphosphino-2-[(S)-α-(N,N-dimethylamino)-o-(dicyclohexylphosphinophenyl)methyl]ferrocene ("Taniaphos T002-2"); (S)-1-diphenylphosphino-2-[α-(S)-hydroxy-(o-diphenylphosphinophenyl)methyl]ferrocene ("Taniaphos OH") and derivatives of this type; (S)-1-diphenylphosphino-2-[α-(S)-methoxy(o-diphenylphosphinophenyl)methyl]ferrocene ("Taniaphos OMe") and derivatives of this type; (R)-1-[(R)-2-(2'-diphenylphosphino phenyl)ferrocenyl]ethyldi(bis-3,5-trifluoromethylphenyl)phosphine ("Walphos W001-1"); (S)-1-[(S)-2-(2'-diphenylphosphinophenyl)ferrocenyl]ethyldi (bis-3,5-trifluoro methylphenyl)phosphine ("Walphos W001-2"); (R)-1-[(R)-2-(2'-diphenylphosphino phenyl)ferrocenyl]ethyldiphenylphosphine ("Walphos W002-1"); (S)-1-[(S)-2-(2'-diphenylphosphinophenyl)ferrocenyl]ethyldiphenylphosphine ("Walphos W002-2"); (R)-1-[(R)-2-(2'-diphenylphosphinophenyl)ferrocenyl]ethyldicyclohexylphosphine ("Walphos W003-1"); (S)-1-[(S)-2-(2'-diphenylphosphinophenyl)ferrocenyl]ethyldicyclohexylphosphine ("Walphos W003-1"); (R)-1-[(R)-2-(2'-di(3,5-dimethyl-4-methoxyphenyl)phosphinophenyl)ferrocenyl]ethyldi(bis-3,5-trifluoromethyl)phenyl)phosphine ("Walphos W005-1"); (S)-1-[(S)-2-(2'-di(3,5-dimethyl-4-methoxyphenyl)phosphinophenyl)ferrocenyl]ethyldi(bis-3,5-trifluoromethylphenyl)phosphine ("Walphos W005-2"); (R)-1-[(R)-2-(2'-diphenylphosphinophenyl)ferrocenyl]ethyldi(3,5-xylyl)phosphine ("Walphos W006-1"); (S)-1-[(S)-2-(2'-diphenylphosphinophenyl)ferrocenyl]ethyldi(3,5-xylyl)phosphine ("Walphos W006-2"); (R)-1-[(R)-2-(2'-dicyclohexylphosphinophenyl)ferrocenyl]ethyldi(3,5-trifluoromethyl)phenyl)phosphine ("Walphos W008-1"); (S)-1-[(S)-2-(2'-dicyclohexylphosphinophenyl)ferrocenyl]ethyldi(3,5-trifluoromethyl)phenyl)phosphine ("Walphos W008-2").

11. The process as claimed in claim 9, wherein $L_D$ is selected from the class of 2-electron donor ligands and encompasses secondary or tertiary phosphines or N-heterocyclic carbene (NHC) ligands.

12. The process as claimed in claim 9, wherein $L_D$ is a solvent ligand selected from the group consisting of acetonitrile ($CH_3CN$), diethyl ether (DEE), water ($H_2O$), acetone, tetrahydrofuran (THF), dioxane, pyridine, imidazole and thiophene.

13. The process as claimed in claim 9, wherein Z is a substituted or unsubstituted cyclic or open-chain dienyl ligand.

14. The process as claimed in claim 9, wherein Z is a ligand selected from the group consisting of 2,4-dimethylpentadiene, 2,3,4-trimethylpentadiene, cycloheptadiene, cyclooctadiene and norbornadiene.

15. The process as claimed in claim 9 which further comprises replacement of at least one neutral ligand $L_D$ by at least one anionic ligand $L_z$ selected from the group consisting of halides and pseudohalides.

16. A ruthenium complex with a chiral ferrocenyldiphosphine ligand that which has bidentate P—P coordination to the Ru(II) obtained by the process as claimed in claim 9.

17. A catalyst for homogeneous asymmetric catalysis for preparing organic compounds comprising the ruthenium complex of claim 1.

18. A catalyst for homogeneous asymmetric catalytic hydrogenation of organic compounds comprising the ruthenium complex of claim 1.

19. A catalyst for enantioselective hydrogenation of C═C, C═O or C═N multiple bonds comprising the ruthenium complex of claim 1.

20. The ruthenium complex as claimed in claim 5, wherein Z is a substituted or unsubstituted pentadienyl or heptadienyl ligand.

21. The process as claimed in claim 13, wherein Z is a substituted or unsubstituted pentadienyl or heptadienyl ligand.

* * * * *